United States Patent [19]

Sollish

[11] 4,056,970
[45] Nov. 8, 1977

[54] ULTRASONIC VELOCITY AND THICKNESS GAGE

[75] Inventor: Bruce D. Sollish, Rehovot, Israel

[73] Assignee: Yeda Research and Development Co., Ltd., Rehovot, Israel

[21] Appl. No.: 627,386

[22] Filed: Oct. 30, 1975

[51] Int. Cl.$^2$ .................................. G01N 29/04
[52] U.S. Cl. ........................ 73/629; 73/622; 73/597
[58] Field of Search ............... 73/67.7, 67.8 R, 67.8 S, 73/67.9

[56] References Cited

U.S. PATENT DOCUMENTS

| | | | |
|---|---|---|---|
| 3,077,769 | 2/1963 | Rankin | 73/67.8 S |
| 3,159,023 | 12/1964 | Steinbrecher | 73/67.8 S |
| 3,269,173 | 8/1966 | Von Ardenne | 73/67.9 |
| 3,603,136 | 9/1971 | Diamond et al. | 73/67.8 R |

Primary Examiner—Richard C. Queisser
Assistant Examiner—John P. Beauchamp
Attorney, Agent, or Firm—Browdy and Neimark

[57] ABSTRACT

An apparatus and method for determining a velocity of propagation and the thickness of different substances such as pipe walls utilizes a transducer connected to an A-scan. This material is placed in a holder between the transducer and a reflecting surface, the holder containing a fluid having a known velocity of propagation. The transducer converts high voltage electrical pulses produced by a generator into ultrasonic vibrations and also converts echo signals received from the reflecting surface and the material back into electrical pulses. A display device connected to the transducer displays these pulses and their exact position on the display device is used to determine the velocity of propagation and the thickness of the material.

6 Claims, 3 Drawing Figures

ULTRASONIC VELOCITY AND THICKNESS GAGE

FIELD OF THE INVENTION

This invention relates to a method and apparatus for measuring propagation times to determine various values, e.g. determining the velocity of propagation and, more particularly, the thickness of certain objects such as pipe walls.

BACKGROUND OF THE INVENTION

An important factor in the quality control of the building and construction industry is the type of materials that are used. Various methods have been devised and devices produced which are useful in detecting certain types of flaws and defects in conduits and pipe walls. One such method has been the utilization of ultrasound waves to determine the composition of these conduits or pipe walls. Ultrasonic imaging is particularly well suited for this determination since it is quite sensitive to composition, density, elasticity and shape. However, prior known devices can determine these values only if certain variables such as wall thickness are already known. For example, present industrial thickness gauges require prior knowledge of the propagation velocity through the material to be tested.

SUMMARY OF THE INVENTION

It is therefore an object of the present invention to overcome the defects of the prior art.

A further object is to provide for the improved measurement of material values based on propagation velocity, but starting with less knowledge about the material to be measured.

Another object of the present invention is to produce a device which can determine the composition of a particular material.

Yet another object of the present invention is to produce a device which determines the velocity of propagation of a particular material.

A still further object of the present invention is to produce a device which determines the thickness of the walls of a certain material such as pipe.

Another object of the present invention is to formulate a method for determining the thickness of pipe walls.

A still further object of the present invention is to formulate a method for determining the velocity of propagation in a certain material.

Another object of the present invention is to formulate a method for determining the presence of defects or flaws in certain materials.

Yet a still further object is to provide for the determination of abnormal body tissue, e.g. malignant growths.

These and other objects of the present invention are fulfilled by a highly reliable method and apparatus for the determination of the velocity of propagation and the thickness measurement of certain materials such as pipe walls. This invention utilizes a transducer which is connected to a generating means for the production of high voltage electrical pulses. This transducer is placed near a holder containing a reflecting surface and also containing a fluid whose velocity of propagation is known. An A-scan is then taken of the reflecting surface and then the material to be tested interposed in front of the reflecting surface. These different scans are displayed in a display means connected to the transducer. The difference between certain echo pulses shown on the display means can be used to determine the velocity of propagation of the material and/or its thickness.

The use of a reflecting surface to provide a reference set of echoes enables calculation of propagation velocity in terms of a simple ratio of two time periods. The thickness of the material tested does not enter into the calculation. Thus, an object of unknown or even varying thickness and unknown or varying velocity of propagation can be characterized in accordance with the present invention.

A device in accordance with the present invention can thickness gage any material without prior knowledge. Therefore, compound structures, complicated alloys, sandwich materials of arbitrary composition, etc., can all be thickness gaged with a device in accordance with the present invention. Similarly in accordance with the present invention one can velocity gage complex structures without prior knowledge of thickness, and the present device can therefore be used in velocity gaging or thickness gaging of objects of varying composition and/or thickness. Thus, there are many applications of the present invention in non-destructive testing, materials evaluation, and medical diagnosis. A particular application in medical diagnosis is in breast cancer diagnosis. With an automated version of the device, a breast can be scanned to give a two-dimensional velocity profile.

For a better understanding of the invention a possible embodiment thereof will now be described with reference to the attached drawing, it being understood that this embodiment is to be intended as merely exemplary and in no way limitative.

DESCRIPTION OF EMBODIMENT

Figure 1:
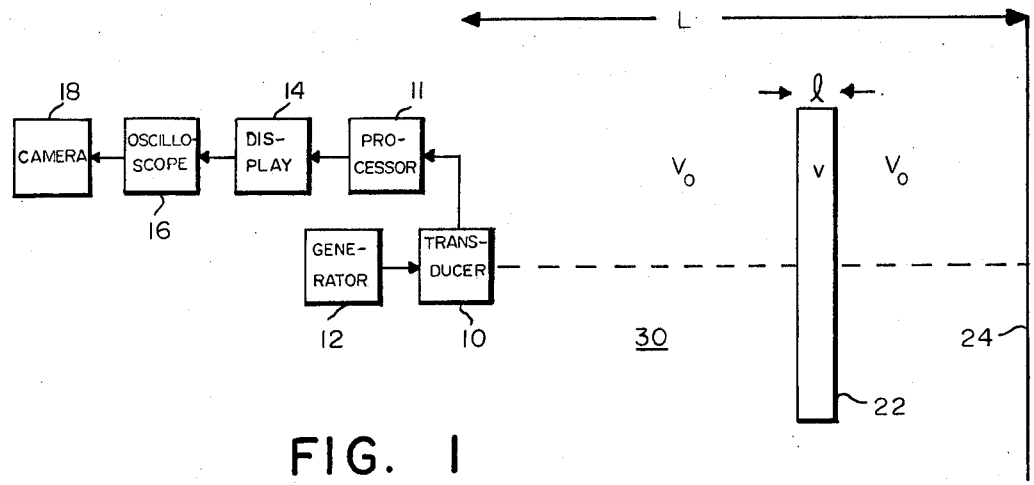
FIG. 1 is a block schematic diagram illustrating the present invention.

FIG. 1 illustrates a device of the present invention which measures the velocity of propagation and the thickness of a sample material 22, such as a pipe wall, having a velocity of propagation V and thickness $l$, placed in a holder containing a fluid 30 having a velocity of propagation $V_o$ between a transducer 10 and a back plate 24 serving as a reflecting surface. The transducer 10 is electrically connected to a generating means 12 such as a pulse generator which produces a high voltage electrical pulse. This pulse is then converted into ultrasonic energy by the transducer 10 which transmits this energy through the fluid medium in the holder, and receives echo pulses when it strikes the back plate 24 and the inner and outer walls of the sample 22.

The transducer 10 converts the ultrasonic echo pulses into electrical pulses and displays them upon a conventional display means 14 such as forms a part of an Automation Industries Reflectoscope model um 775 after they have been decoded by a conventional processor 11 contained within the Reflectoscope. The Reflectoscope itself, as pointed out above, may embody the processor 11 and the generator 12 the processor 11 being constituted as a radio frequency amplifier, a detector and a video amplifier. An oscilloscope 16, such as a Tectronix monitor oscilloscope, is slaved to the display 14 thus enabling the wave form to be photographed using a Polaroid or other still or movie camera 18.

Figure 2:
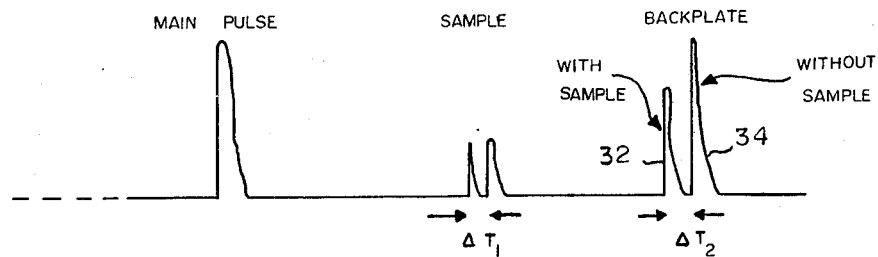
FIG. 2 shows a sample output in accordance with the present invention.

In order to determine the velocity of propagation or the wall thickness, a scan must be first taken of the holder without the sample and then a scan is taken with the sample 22 inserted into the fluid medium 30 between the transducer 10 and the back plate 24. A sample display is shown in FIG. 2 with $\Delta T_1$ denoting the displacement between the inner and outer walls of the material 22, and $\Delta T_2$ denoting the position of the back plate with the sample 22 in place (reflected pulse 32) and the position of the back plate without the sample 22 in place (reflected pulse 34). If the backplate echo is displaced to the left when the sample is inserted, $\Delta T_2$ is negative; if the backplate echo is displaced to the right when the sample is inserted, $\Delta T_2$ is positive. The following equations then apply:

$$\Delta T_1 = 2l/V \tag{1}$$

$$\Delta T_2 = \frac{2(L-l)}{V_o} + \frac{2l}{V} - \frac{2L}{V_o} \tag{2}$$

$$= 2l\left(\frac{1}{V} - \frac{1}{V_o}\right)$$

From equations (1) and (2)

$$V/V_o = 1 - \Delta T_2/\Delta T_1 \tag{3}$$

and $$l = l_o(1 - \Delta T_2/\Delta T_1) \tag{4}$$

where $$l_o = V_o \Delta T_1/2 \tag{5}$$

For a linear display, the quantity $\Delta T_2/\Delta T_1$ is the ratio of the displayed backplate echo displacement to the displayed sample thickness. If, in addition, the reflectoscope 14 is calibrated properly for the particular fluid medium 30, the term $l_0$ is read directly from the display (i.e., equation (5) is then performed by the reflectoscope itself). To avoid problems with multiple echoes, the transducer-sample distance should be larger than the sample-to-back plate distance. On the other hand, the sample-back plate distance should be large enough so that multiple echoes originating within the sample do not overlap the displaced echo of the back plate 24.

Figure 3:
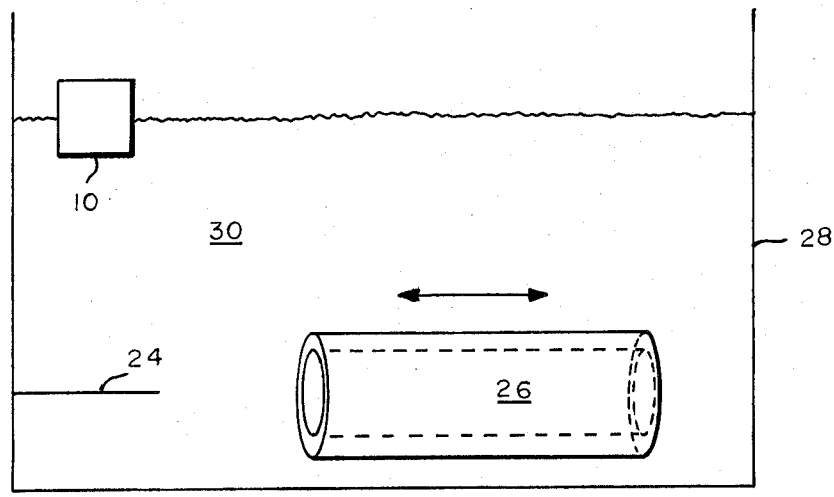
FIG. 3 is a diagrammatical view of an embodiment showing the transducer, back plate and sample.

An exemplary assembly of the present device is shown in FIG. 3 for measuring pipe thickness and propagation velocity. This assembly shows the transducer 10 which is partly immersed in a holder 28 containing water as the fluid medium 30 which has a velocity of propagation of 1.48 = $10^3$ m/sec. A polyvinyl chloride back plate 24 is used. Although many types of transducers can be used, it has been found that a 5 mHz flat transducer having a 1 cm beam width performed with quite satisfactory results.

The A-scan apparatus is activated and a measurement is taken of the back plate echo without the pipe 26 being placed between the transducer 10 and the back plate 24. The position of this echo is displayed on the reflectoscope 14 and is brought to a convenient location on its display screen. The particular reflectoscope which was used in this experiment was calibrated in terms of one division equalling 2 mm.

The pipe 26 is then slid into position between the back plate 24 and the transducer 10 and the new position of the back plate echo 32 and the position of the echo corresponding to the outer and inner walls of the pipe 26 are recorded. Sample readings are shown in FIG. 2.

From these four echo locations, the velocity of propagation ratio $V/V_o$ is ascertained. Both ends of the pipe 26 having a wall thickness $l$ of approximately 5 mm was used in this experiment with the results shown in Table I.

TABLE I

First end of pipe 26

| Measurement | $V/V_o$ | $l$ |
|---|---|---|
| 1. | 2.23 | 4.9 mm |
| 2. | 2.27 | 5.0 |
| 3. | 2.23 | 4.9 |
| 4. | 2.25 | 4.5 |
| 5. | 2.24 | 4.7 |

Second end of pipe 26

| Measurement | $V/V_o$ | $l$ |
|---|---|---|
| 1. | 2.13 | 5.1 |
| 2. | 2.17 | 5.2 |
| 3. | 2.17 | 5.0 |
| 4. | 2.23 | 4.9 |
| 5. | 2.08 | 5.0 |
| 6. | 2.13 | 5.1 |

This procedure was repeated for a number of points at each of the two ends of the pipe and the average velocity of propagation of the pipe and standard deviation were then calculated for each of these two ends.

For end No. 1, the average velocity ratio was $\overline{V_1}/V_0 = 2.24$ with a standard deviation $\sigma_1 = 0.017$. In absolute terms, since $V_0 = 1.48 \times 10^3$ m/sec., $\overline{V_1} = 3,321$ m/sec. and $\sigma = 25$ m/sec. Making the same calculations for end two of the pipe 26, $\overline{V_2}/V_0 = 2.15(\sigma_2 = 0.051)$ and therefore $\overline{V_2} = 3,185$ m/sec. ($\sigma_2 = 75$ m/sec.). Since $\overline{V_1} - \overline{V_2} \cong 2\sigma_2$, the difference in propagation velocity are statistically significant. Therefore, it is shown that the velocity of propagation through inhomogeneous or heterogeneous pipe can be readily measured and the difference in propagation velocity of only a few percentages can be detected. Accordingly, this type of velocity gaging can be useful in detecting certain types of flaws and defects in the pipe wall.

Similarly, this type of velocity gaging can be useful in medical diagnoses and has particular application in determining the presence of breast cancer. The breast can be scanned using the A-scan to obtain a velocity profile and since the lesions exhibit different velocity of propagations than the surrounding normal tissue, the presence of these lesions can be so detected, the procedure also giving the X-Y coordinates of the lesion. In this situation, the breast is not placed in the holder, but rather the transducer can be immersed in a water bath and placed against a rubber membrane or other suitable substance with the breast placed on the other side of this membrane. In this case, a reflecting surface external to the body can be used for the reference data.

For flat samples, the far end of the sample can be placed against the backplate. In this case, the second sample echo and displaced backplate echo coincide. This may simplify the measurement procedure.

The present invention has numerous advantages: the principle of the device is simple, and in practice the implementation is also quite simple, using for the most part conventional ultrasonic equipment. Measurements of propagation velocity and thickness are accurate to 1%, with laboratory prototype and with automated digital readout model measurements even more accurate.

Although this invention has been described with particular emphasis on its use of detecting flaws and other defects in pipe walls and also in diagnosing the presence of breast cancer, the scope of this invention should not be construed to be so limited. For example, with only a slight modification of the equipment, the presence of tumors in other parts of the body can be detected.

The composition of the back plate 24 is not critical; any material which will reflect the pulses is adequate. Similarly, the nature of the fluid 30 is also not critical, so long as its velocity of propagation is known. Even if the velocity of propagation of the medium is not known, the procedure described will still give an accurate measurement of *relative* propagation velocity.

The measurements of the times $\Delta T_1$ and $\Delta T_2$ and the computation of the propagation velocity and thickness can be accomplished either manually or automatically by the appropriate electronic circuitry.

It will be obvious to those skilled in the art that various changes may be made without departing from the scope of the invention and the invention is not to be considered limited to what is shown in the drawings and described in the specification.

What is claimed is:

1. A method for determining the velocity of propagation of a particular material, comprising the steps of:

providing a reflecting surface in a fluid medium having a known velocity of propagation;

recording the position in time of an echo received from said reflecting surface utilizing a transducer to create at least one ultrasonic pulse which is reflected off said reflecting surface;

placing the material to be tested in said fluid between said transducer and said reflecting surface;

transmitting at least one ultrasonic pulse from the transducer and receiving echoes of said pulse reflected from said material and from said reflecting surface;

recording the position in time of the echoes corresponding to the anterior and posterior surfaces of said material and the new position in time of the echo from said reflecting surface; and determining the velocity of propagation of said material by utilizing the positions in time of said echoes, according to the equation $$V/V_o = 1 - \Delta T_2/\Delta T_1$$

where $V$ is the propagation velocity in the material to be tested, $V_o$ is the propagation velocity in the fluid medium, $\Delta T_2$ is the round trip propagation time from the transducer to the reflecting surface with the material to be tested positioned somewhere in between, minus the round trip propagation time from the transducer to the reflecting surface with said material removed, and $\Delta T_1$ is the round trip propagation time between the anterior and posterior surfaces of the material to be tested.

2. A method for determining the thickness of a particular material, comprising the steps of:

providing a reflecting surface in a fluid medium having a known velocity of propagation;

recording the position in time of an echo received from said reflecting surface utilizing a transducer to create at least one ultrasonic pulse which is reflected off said reflecting surface;

placing the material to be tested between said transducer and said reflecting surface in said fluid;

transmitting at least one ultrasonic pulse from the transducer and receiving echoes of said pulse reflected from said material and from said reflecting surface;

recording the positions in time of the echoes corresponding to the anterior and posterior surfaces of said material and the new position in time of the echo from said reflecting surface; and determining the thickness of said material by utilizing the positions in time of said echoes, according to the equation $$l = l_o(1 - \Delta T_2/\Delta T_1)$$

where $l$ = actual thickness of the material to be tested, $l_o = V_o \Delta T_1/2$, the apparent thickness of the material, as if the propagation velocity were $V_o$, $V_o$ is the propagation velocity in the fluid medium, $\Delta T_2$ is the round trip propagation time from the transducer to the reflecting surface with the material to be tested positioned somewhere in between, minus the round trip propagation time from the transducer to the reflecting surface with said material removed, and $\Delta T_1$ is the round trip propagation time between the anterior and posterior surfaces of the material to be tested.

3. A method for determining the presence of a lesion in a human breast comprising the steps of:

providing a reflecting surface in a fluid medium having a known velocity of propagation;

recording the position in time of an echo received from said reflecting surface utilizing a transducer to create at least one ultrasonic echo which is reflected off said reflecting surface;

placing the breast between said transucer and said reflecting surface;

displacing the transducer in a plane parallel to the reflecting surface in steps;

determining the propagation velocity in the breast at each new position of the transducer according to the equation $V/V_o = 1 - \Delta T_2/\Delta T_1$, utilizing echoes from the anterior and posterior surface of the breast and the echo from the reflecting surface and repeating the above two steps unitl the entire breast is scanned;

where $V$ is the propagation velocity in the breast to be tested, $V_o$ is the propagation velocity in the fluid medium, $\Delta T_2$ is the round trip propagation time from the transducer to the reflecting surface with the breast to be tested in between minus the round trip propagation time from the transducer to the reflecting surface with the breast removed from the propagation path, and $\Delta T_1$ is the round trip propagation time between the anterior and posterior surfaces of the breast tested;

whereby the presence of one or more lesions beneath a two-dimensional plane can be determined since the velocity of propagation in the lesions differs from that of the remainder of the breast.

4. In an apparatus for measuring characteristics of materials utilizing ultrasound comprising a transducer, means to power said transducer, and means for collecting information concerning the characteristics of the material tested from ultrasound emitted by said transducer, the improvement comprising:

an ultrasound reflector disposed opposite said transducer and at any downstream location from the material to be tested, fluid having a known velocity of propagation between said transducer and said reflector, and wherein said means for collecting include means for determining difference in transit time of ultrasound to and from said reflector with and without the material in said fluid and for determining transit times of ultrasound to and from anterior and posterior surfaces of said material when present in said fluid, according to the equation $$V/V_o = 1 - \Delta T_2/\Delta T_1$$

where $V$ is the propagation velocity in the material to be tested, $V_o$ is the propagation velocity in the fluid medium, $\Delta T_2$ is the round trip propagation time from the transducer to the reflecting surface with the material to be tested positioned somewhere in between, minus the round trip propagation time from the transducer to the reflecting surface with said material removed, and $\Delta T_1$ is the round trip propagation time between the anterior and posterior surfaces of the material to be tested.

5. An improved apparatus according to claim 4, including display means coupled to said transducer for displaying converted mechanical energy received from said reflector and said surfaces of said material.

6. An improved apparatus according to claim 5, further including a recordation means operatively connected to said display means for producing a permanent record of the converted mechanical energy shown on said display means.

* * * * *

UNITED STATES PATENT AND TRADEMARK OFFICE
CERTIFICATE OF CORRECTION

PATENT NO. : 4,056,970
DATED : November 8, 1977
INVENTOR(S) : Bruce D. SOLLISH

It is certified that error appears in the above-identified patent and that said Letters Patent are hereby corrected as shown below:

Column 2, line 61, "um" should read --UM--

Column 3, line 54, "$1.48 = 10^3 m/sec$" should read --$1.48 \times 10^3 m/sec$--

Signed and Sealed this

Thirteenth Day of June 1978

[SEAL]

Attest:

RUTH C. MASON
Attesting Officer

DONALD W. BANNER
Commissioner of Patents and Trademarks